(12) United States Patent
Domoto

(10) Patent No.: US 10,888,217 B2
(45) Date of Patent: Jan. 12, 2021

(54) IMAGING MODULE APPLICABLE TO HEAD-SWING ENDOSCOPE

(71) Applicant: FUJIKURA LTD., Tokyo (JP)

(72) Inventor: Kazuhiro Domoto, Sakura (JP)

(73) Assignee: Fujikura Ltd., Tokyo (JP)

( * ) Notice: Subject to any disclaimer, the term of this patent is extended or adjusted under 35 U.S.C. 154(b) by 0 days.

(21) Appl. No.: 16/246,144

(22) Filed: Jan. 11, 2019

(65) Prior Publication Data

US 2019/0231180 A1   Aug. 1, 2019

(30) Foreign Application Priority Data

Jan. 26, 2018   (JP) .................................. 2018-011813

(51) Int. Cl.
| | | |
|---|---|---|
| *A61B 1/05* | (2006.01) | |
| *H04N 5/247* | (2006.01) | |
| *A61B 1/00* | (2006.01) | |
| *H04N 5/225* | (2006.01) | |
| *H01L 27/146* | (2006.01) | |

(52) U.S. Cl.
CPC ............ *A61B 1/05* (2013.01); *A61B 1/00114* (2013.01); *A61B 1/00124* (2013.01); *A61B 1/051* (2013.01); *H01L 27/14618* (2013.01); *H04N 5/2253* (2013.01); *H04N 5/2257* (2013.01); *H04N 5/247* (2013.01); *H04N 2005/2255* (2013.01)

(58) Field of Classification Search
CPC ....................... H01L 27/14618; H04N 5/2253; H04N 5/247; H04N 5/2257
See application file for complete search history.

(56) References Cited

U.S. PATENT DOCUMENTS

| | | | |
|---|---|---|---|
| 6,086,528 A | 7/2000 | Adair | |
| 2011/0249106 A1* | 10/2011 | Makino | .................. H05K 1/189 348/76 |
| 2016/0287060 A1 | 10/2016 | Usuda et al. | |
| 2017/0153441 A1* | 6/2017 | Ishizuka | .............. H04N 5/2253 |
| 2018/0132704 A1* | 5/2018 | Yamada | ............. A61B 1/00128 |

FOREIGN PATENT DOCUMENTS

| | | |
|---|---|---|
| EP | 2781183 A1 | 9/2014 |
| JP | 2006-109097 A | 4/2006 |
| JP | 2013103011 A | 5/2013 |
| JP | 2015062555 A | 4/2015 |
| JP | 2016131709 A | 7/2016 |
| JP | 2016190007 A | 11/2016 |

* cited by examiner

*Primary Examiner* — Antoinette T Spinks
(74) *Attorney, Agent, or Firm* — Osha Bergman Watanabe & Burton LLP

(57) ABSTRACT

An imaging module includes: an image-sensing device that includes a terminal group having a plurality of image-sensing terminals; a flexible substrate that includes: a first surface, a second surface on the opposite side of the first surface, and conductors disposed on the first surface and the second surface; a single-core wire unit that: is disposed between the image-sensing device and the flexible substrate, electrically connects the terminal group to the conductors, and includes a plurality of flexible single-core wires; and a coaxial cable that is connected to the conductor.

9 Claims, 5 Drawing Sheets

FIG. 4A
FIG. 4B
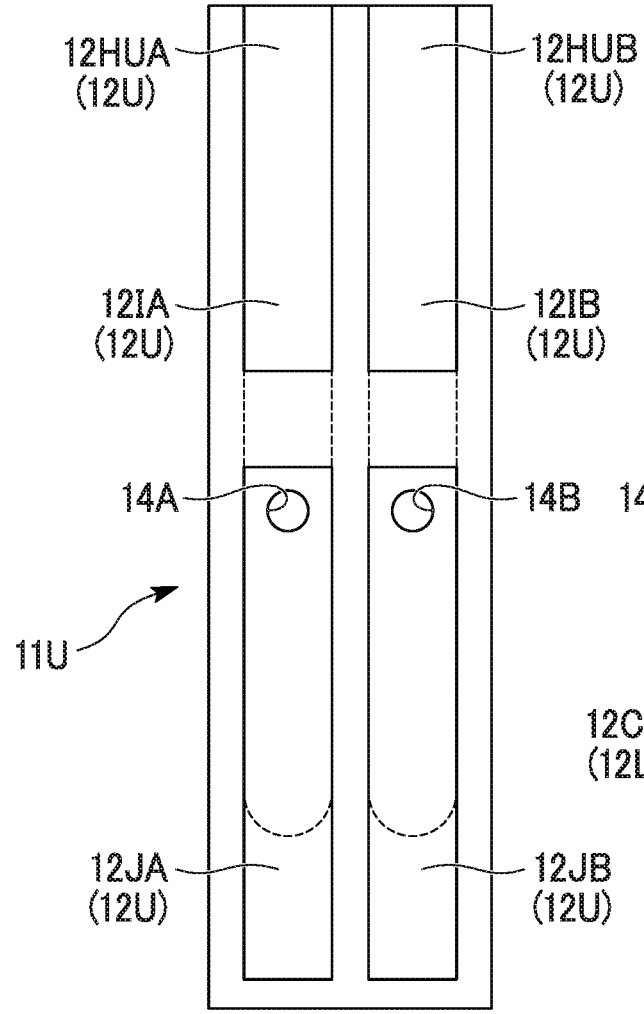
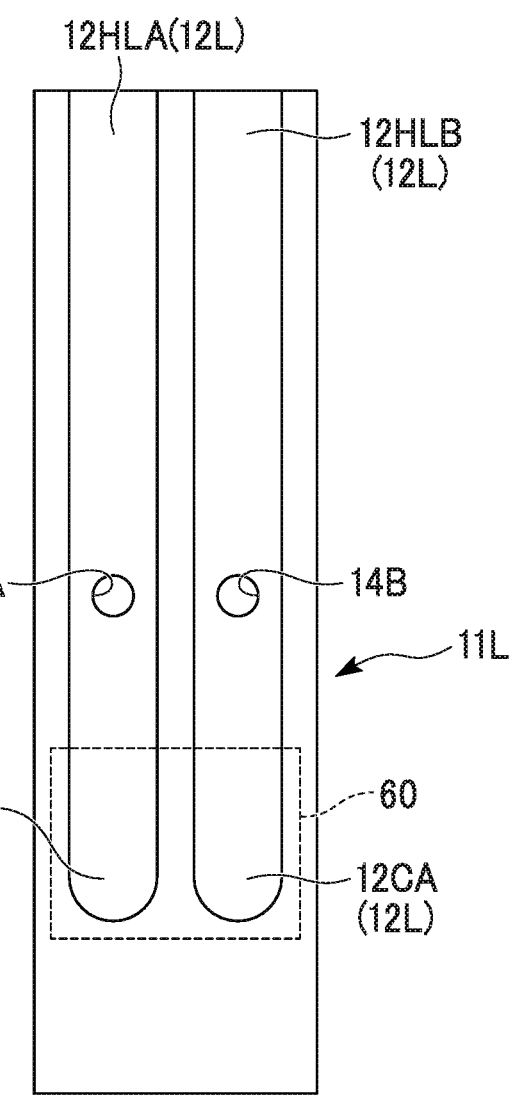
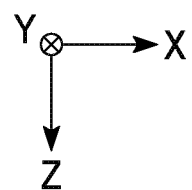

IMAGING MODULE APPLICABLE TO HEAD-SWING ENDOSCOPE

CROSS REFERENCE TO RELATED APPLICATIONS

This application claims priority from Japanese Patent Application No. 2018-011813 filed on Jan. 26, 2018, which is incorporated herein by reference in its entirety.

TECHNICAL FIELD

The present invention relates to an imaging module.

BACKGROUND

An imaging module having a configuration in which a solid-state image sensing device (hereinbelow, may be simply referred to as an image-sensing device) is electrically connected to an end of an electrical cable with a wiring substrate interposed therebetween is often employed in electronic endoscopes (for example, Japanese Unexamined Patent Application, First Publication No. 2006-109097).

In this kind of imaging module, a plurality of ends of the electrical cable are electrically connected to wiring of the wiring substrate, and each electrical cable is electrically connected to the image-sensing device via the wiring of the wiring substrate.

In an imaging device such as an endoscope using the aforementioned imaging module, a configuration is often employed in which a plurality of electrical cables connected to an imaging module and a wiring substrate of the imaging module are accommodated in a tube. Furthermore, an back end that is opposite to the imaging module side of the electrical cable of this imaging device is drawn from the tube and is electrically connected to an image processing device that receives imaging signals from the electrical cable and displays an image on a display device such as a monitor.

In recent years, an endoscope having a further small diameter is required, as an electrical cable used in a transmission path of the endoscope, an ultrafine electrical cable is employed. However, a pixel signal transmitted through the above-described electrical cable easily receives noise from the outside in the transmission path. Accordingly, it is necessary that a Micro ultrafine coaxial wire which is not a single electrical cable and is configured to include an internal conductor and an external conductor is used in the transmission path.

On the other hand, in order to obtain electrical connection with respect to terminals formed on a substrate or the like, approximately 1 mm is required at a minimum as an exposed conductor length of each of the internal conductor and the external conductor of the coaxial wire. Consequently, a length of an endoscope (length in vertical direction with respect to an imaging surface of an image-sensing device) includes a length of a lens, a thickness of the image-sensing device, and an exposed conductor length of the coaxial wire.

For example, in an imaging module having a flexible substrate on which an image-sensing device is mounted or an imaging module having a three-dimensional wiring substrate on which an image-sensing device is mounted, a length (rigid portion length) from a lens end to a soldered portion of a signal cable is large. For a specific example, a rigid portion length of the configuration in which an image-sensing device is mounted on a flexible substrate is approximately 4.8 mm, and a rigid portion length of the configuration in which an image-sensing device is mounted on a three-dimensional wiring substrate is approximately 4.1 mm. In the case of applying the imaging module having the above-described rigid portion length to a head-swing endoscope or the like, a head swing radius increases, and it is difficult to use the endoscope in a further fine and narrow environment.

Moreover, although a method of directly solder-mounting a coaxial wire on an image-sensing device without use of the flexible substrate or the three-dimensional wiring substrate may be considered, it is necessary to separate one coaxial wire into an internal conductor and an external conductor and carry out operation of connecting the internal conductor and the external conductor which were separated therefrom to an extremely small image-sensing device. In this case, a level of difficulty of the connection operation is high, and it is difficult to economically manufacture imaging modules.

In addition, since a connection portion to which a coaxial wire and a terminal are to be connected is hardened due to solder or conductive adhesive, in the case of bending the connection portion, there is an extremely high possibility that a conductor of the coaxial wire is broken. Accordingly, in the case of applying a conventional imaging module to the above-described head-swing endoscope or the like, a movable region at the distal end of the endoscope is limited.

SUMMARY

One or more embodiments provide an imaging module which is applicable to a head-swing endoscope that has a small diameter, achieves a large movable region, and can be used in a small head swing radius.

An imaging module according to one or more embodiments of the invention includes: an image-sensing device that includes a terminal group having a plurality of image-sensing terminals; a flexible substrate that includes: a first surface, a second surface located on the opposite side of the first surface, and conductors provided on the first surface and the second surface; a single-core wire unit that is located between the image-sensing device and the flexible substrate, electrically connects the terminal group to the conductor, and includes a plurality of single-core wires each having flexibility; and a coaxial cable that is connected to the conductor.

The imaging module according to one or more embodiments of the invention may further include: solder that connects the terminal group to the single-core wire unit; solder that connects the single-core wire unit to the conductor; and solder that connects the conductor to the coaxial cable.

The imaging module according to one or more embodiments of the invention may further include resin that coats: the solder that connects the terminal group to the single-core wire unit; the solder that connects the single-core wire unit to the conductor; and the solder that connects the conductor to the coaxial cable.

In the imaging module according to one or more embodiments of the invention, the terminal group of the image-sensing device may have a first image-sensing terminal and a second image-sensing terminal, the conductor of the flexible substrate may have a first conductor provided on the first surface and a second conductor provided on the second surface, and the single-core wire unit may have a first single-core wire that electrically connects the first image-sensing terminal to the first conductor and a second single-core wire that electrically connect the second image-sensing terminal to the second conductor.

In the imaging module according to one or more embodiments of the invention, the coaxial cable may have two coaxial cables disposed on the first surface, each of the two coaxial cables may include an internal conductor and an external conductor, the flexible substrate may include: an external conductor terminal formed on the first surface; and a through conductor that penetrates through the flexible substrate and electrically connects the external conductor terminal to the second conductor, the internal conductor may be electrically connected to the first image-sensing terminal via the first conductor and the first single-core wire, and the external conductor may be electrically connected to the second image-sensing terminal via the external conductor terminal, the through conductor, the second conductor, and the second single-core wire.

The imaging module according to one or more embodiments of the invention may further include a condenser provided on at least one of the first surface and the second surface of the flexible substrate.

As described above, according to one or more embodiments of the invention, it is possible to provide an imaging module which is applicable to a head-swing endoscope that has a small diameter, achieves a large movable region, and can be used in a small head swing radius.

BRIEF DESCRIPTION OF THE DRAWINGS

FIG. 4A is a plan view showing a conductive pattern formed on a flexible substrate constituting the imaging module according to one or more embodiments of the invention and is an explanatory view showing a connection structure between a single-core wire unit and a signal cable.

FIG. 4B is a plan view showing a conductive pattern formed on the flexible substrate constituting the imaging module according to one or more embodiments of the invention and is an explanatory view showing the connection structure between the single-core wire unit and the signal cable.

DETAILED DESCRIPTION

Figure 1:
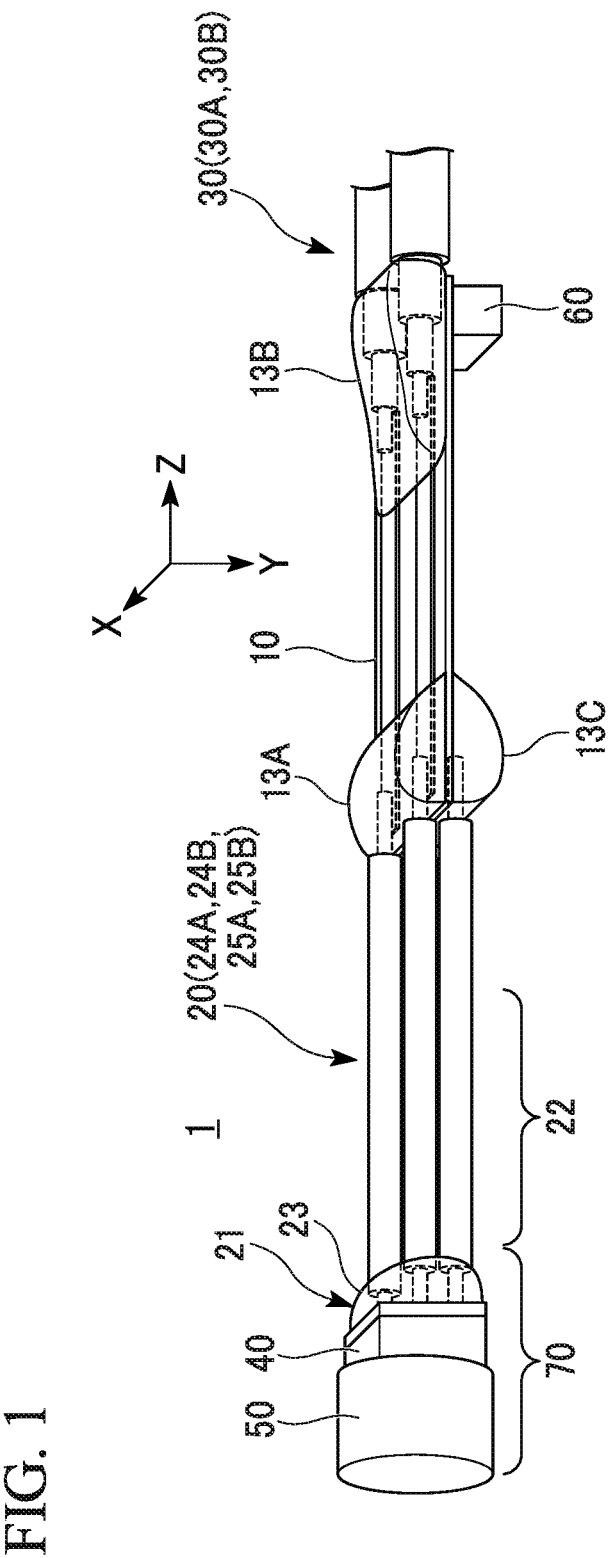
FIG. 1 is a perspective view showing a schematic configuration of an imaging module according to one or more embodiments of the invention.

Hereinafter, one or more embodiments of the invention will be described with reference to FIGS. 1 to 5.

In the drawings showing embodiments of the invention, in order for the respective components to be of understandable size in the drawings, the dimensions and the proportions of the components are modified as needed compared with the real components.

As shown in FIG. 1, an imaging module 1 according to one or more embodiments of the invention includes a flexible substrate 10, a single-core wire unit 20, a signal cable 30 (coaxial cable), a solid-state image sensing device 40 (image-sensing device), a lens unit 50, and a condenser 60.

A region represented by reference numeral 70 is a rigid portion. The rigid portion 70 corresponds to the lens unit 50, the solid-state image sensing device 40, and a cable end 21L of the single-core wire unit 20. The total length of the lens unit 50 and the solid-state image sensing device 40 is approximately 1.7 mm, the length of the cable end 21L is approximately 0.5 mm. Therefore, the length of the rigid portion 70 (rigid portion length) is approximately 2.2 mm.

A region represented by reference numeral 22 is a region at which a plurality of single-core wires constituting the single-core wire unit 20 bend, that is, a movable region. More specifically, as seen from the side surface and the upper surface of the imaging module 1 (in the X-direction and the Y-direction), the imaging module 1 can bend at ±90 degrees with respect to the extending direction thereof (Z-direction) in the movable region 22.

(Flexible Substrate 10)

The flexible substrate 10 includes: a first surface 11U (upper surface); a second surface 11L located on the opposite side of the first surface 11U (lower surface); a first conductor 12U (conductor 12) provided on the first surface 11U; and a second conductor 12L (conductor 12) provided on the second surface 11L.

Furthermore, the flexible substrate 10 includes: an external conductor terminal 12J (conductor 12) formed on the first surface 11U; and a through conductor 14 that penetrates through the flexible substrate 10 and electrically connects the external conductor terminal 12J to the second conductor 12L.

The single-core wire unit 20 and the conductor 12 are connected to each other by soldering, and the conductor 12 and the signal cable 30 are connected to each other by soldering.

A cable end 21R of a first single-core wire 24 (which will be described below) constituting the single-core wire unit 20 is electrically connected to the first conductor 12U via solder 15. An internal conductor 31 (which will be described below) constituting the signal cable 30 is electrically connected to the first conductor 12U via solder 16. An external conductor 33 (which will be described below) constituting the signal cable 30 is electrically connected to the external conductor terminal 12J via solder 17. A cable end 21R of a second single-core wire 25 (which will be described below) constituting the single-core wire unit 20 is electrically connected to the second conductor 12L via solder 18.

Particularly, in one or more embodiments, the signal cable 30 is disposed only on one of the surfaces (first surface 11U) of the flexible substrate 10, electrical connection between the internal conductor 31 and the first conductor 12U and electrical connection between the external conductor 33 and the external conductor terminal 12J are carried out on the first surface 11U.

Note that, conductive patterns of the first conductor 12U, the second conductor 12L, the external conductor terminal 12J, and the through conductor 14 will be described below.

Moreover, the solders 15 to 18 are covered with resist (resin), and the strength of the electrical connection structure is reinforced by the solders 15 to 18.

A first resist 13A is provided on the first surface 11U of the flexible substrate 10 so as to cover the solder 15 formed on the first conductor 12U. A second resist 13B is provided so as to cover the solder 16 formed on the first conductor 12U and the solder 17 formed on the external conductor terminal 12J. A third resist 13C is provided so as to cover the solder 18 formed on the second conductor 12L.

In FIG. 1, as seen in the direction from the solid-state image sensing device 40 to the lens unit 50, the signal cable 30 is disposed within an outline of the solid-state image sensing device 40 on a plane of projection, and the signal cable 30 does not partially protrude from the outline of the solid-state image sensing device 40 on a plane of projection. (Solid-State Image Sensing Device 40 and Lens Unit 50)

Figure 3A:
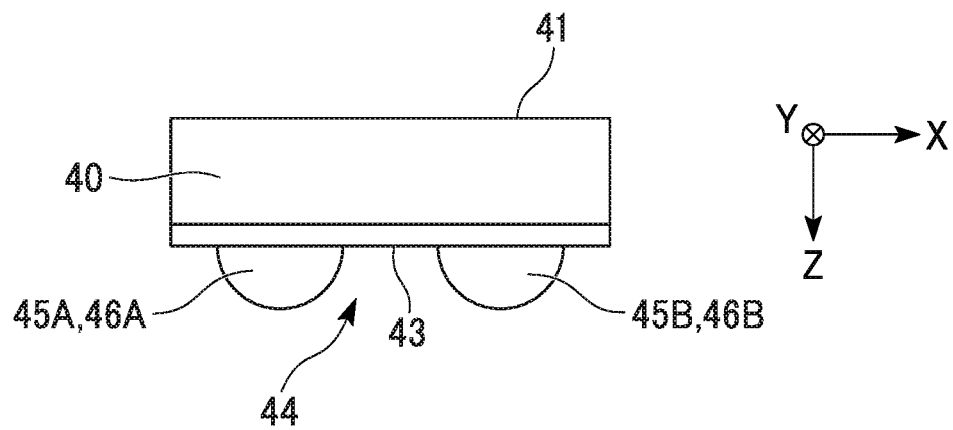
FIG. 3A is a view showing a schematic configuration of a solid-state image sensing device constituting the imaging module according to one or more embodiments of the invention and is an explanatory view showing a connection structure between the solid-state image sensing device and a single-core wire unit.
Figure 3B:
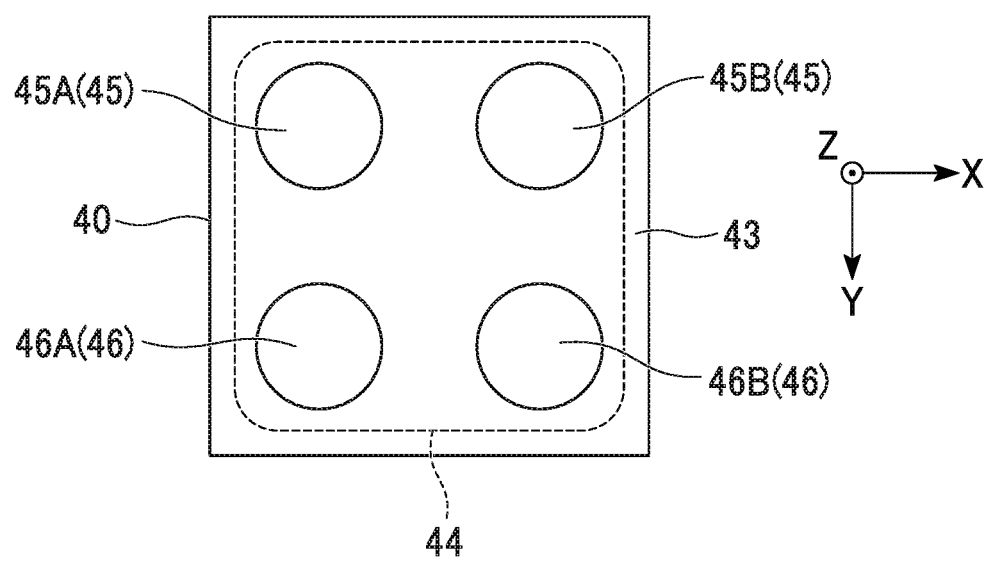
FIG. 3B is a view showing a schematic configuration of the solid-state image sensing device constituting the imaging module according to one or more embodiments of the invention and is an explanatory view showing the connection structure between the solid-state image sensing device and the single-core wire unit.

FIG. 3A is a side view showing a schematic configuration of the solid-state image sensing device 40, and FIG. 3B is a bottom view showing a schematic configuration of the solid-state image sensing device 40.

The solid-state image sensing device 40 includes a light-receiving face 41, a terminal surface 43 located on the opposite side of the light-receiving face 41, and a terminal group 44 provided on the terminal surface 43. The terminal group 44 has a plurality of image-sensing terminals. In one or more embodiments, the number of the image-sensing terminals is four, that is, two first image-sensing terminals 45 (45A, 45B) and two second image-sensing terminals 46 (46A, 46B) are provided on the terminal surface 43.

The lens unit 50 is connected to the light-receiving face 41, and a lens unit such as an object lens is mounted on the lens unit 50. As the solid-state image sensing device 40, for example, a CMOS (complementary metal oxide semiconductor) may be used.
(Single-Core Wire Unit 20)

Figure 2:
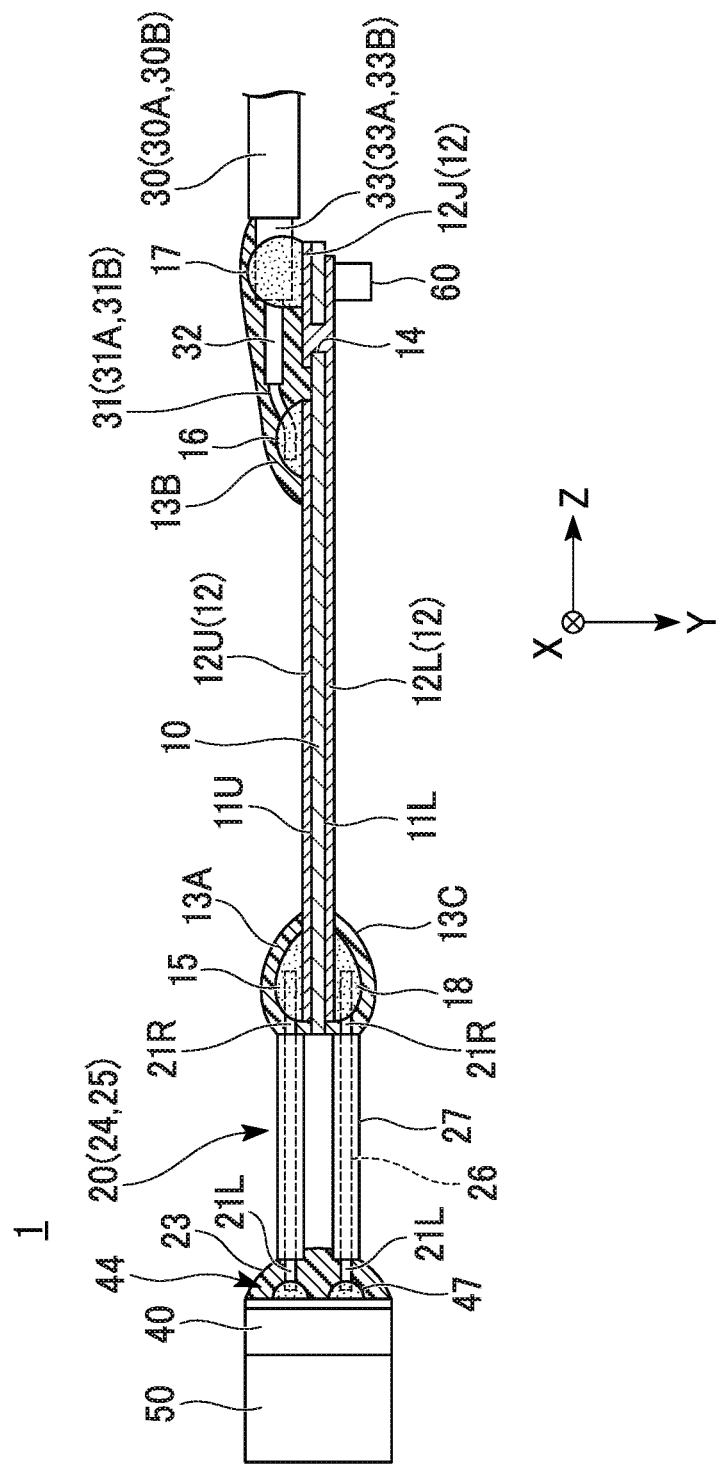
FIG. 2 is an enlarged cross-sectional view showing a schematic configuration of the imaging module according to one or more embodiments of the invention.

As shown in FIGS. 1 and 2, the single-core wire unit 20 is located between the solid-state image sensing device 40 and the flexible substrate 10 and electrically connects the terminal group 44 to the conductor 12. The single-core wire unit 20 is configured to include a plurality of single-core wires having flexibility. In one or more embodiments, the number of single-core wires corresponds to the number of the image-sensing terminals and is four. That is, the single-core wire unit 20 is constituted of the two first single-core wires 24 (24A, 24B) and the two second single-core wires 25 (25A, 25B). The first single-core wire 24 electrically connects the first image-sensing terminal 45 to the first conductor 12U. The second single-core wire 25 electrically connects the second image-sensing terminal 46 to the second conductor 12L.

Each of the single-core wires 24 and 25 includes: one conductive wire 26; and an insulating coating 27 that coats the outside of the conductive wire 26. The insulating coating 27 is removed at both ends of each of the single-core wires 24 and 25. Consequently, each of the single-core wires 24 and 25 includes the cable end 21L (first cable end) and the cable end 21R (second cable end) at which the conductive wire 26 is exposed from the insulating coating 27.

An outer diameter of each of the single-core wires 24 and 25 (outer diameter of the insulating coating 27) is, for example, less than or equal to 0.4 mm. A length of each of the single-core wires 24 and 25 (length the insulating coating 27) is, for example, 1 cm to 5 cm.

As a result of shortening the length of the single-core wire so as to be the aforementioned length, it is possible to reliably transmit a signal from the solid-state image sensing device 40 to the flexible substrate 10 without being mostly affected by noise.

The single-core wire unit 20 having the above-described configuration is connected to the terminal group 44 of the solid-state image sensing device 40 shown in FIGS. 3A and 3B by solder 47.

In the soldered connection structure, the cable end 21L of the first single-core wire 24A is electrically connected to the first image-sensing terminal 45A, the cable end 21L of the first single-core wire 24B is electrically connected to the first image-sensing terminal 45B, the cable end 21L of the second single-core wire 25A is electrically connected to the second image-sensing terminal 46A, and the cable end 21L of the second single-core wire 25B is electrically connected to the second image-sensing terminal 46B.

Furthermore, the solder 47 is covered with fourth resist 23 (resin), and the strength of the electrical connection structure is reinforced by the solder 47.
(Conductive Pattern of Flexible Substrate 10)

FIGS. 4A and 4B are views each showing a conductive pattern formed on the flexible substrate 10.

FIG. 4A shows a conductive pattern of the first conductor 12U formed on the first surface 11U of the flexible substrate 10. FIG. 4B shows a conductive pattern of the second conductor 12L formed on the second surface 11L of the flexible substrate 10. FIG. 4B is not a bottom view showing the second surface 11L but is a projection view as seen from the first surface 11U shown in FIG. 4A. Consequently, the portion indicated by the broken line shown in FIG. 4A corresponds to the portion indicated by the solid line shown in FIG. 4B.

Note that, as shown in FIG. 1, although the first resist 13A, the second resist 13B, and the third resist 13C are formed on the first surface 11U and the second surface 11L of the flexible substrate 10, the resists 13A, 13B, and 13C are omitted in FIGS. 4A and 4B.

Reference numeral 12JA corresponds to the external conductor terminal 12J and is a terminal to which an external conductor 33A (33) of a first coaxial cable 30A (which will be described below) is connected to via the solder 17 (hereinbelow, it will be referred to as an external conductor terminal 12JA).

Reference numeral 12JB corresponds to the external conductor terminal 12J and is a terminal to which an external conductor 33B (33) of a second coaxial cable 30B (which will be described below) is connected to via the solder 17 (hereinbelow, it will be referred to as an external conductor terminal 12JB).

Reference numeral 12IA is a terminal to which an internal conductor 31A (31) of the first coaxial cable 30A is connected via the solder 16 (hereinbelow, it will be referred to as an internal conductor terminal 12IA).

Reference numeral 12IB is a terminal to which an internal conductor 31B (31) of the second coaxial cable 30B is connected via the solder 16 (hereinbelow, it will be referred to as an internal conductor terminal 12IB).

The internal conductor terminals 12IA and 12IB constitute part of the first conductor 12U.

Reference numeral 12HUA is a terminal to which the cable end 21R of the first single-core wire 24A is connected (hereinbelow, it will be referred to as an electrical cable terminal 12HUA).

Reference numeral 12HUB is a terminal to which the cable end 21R of the first single-core wire 24B is connected (hereinbelow, it will be referred to as an electrical cable terminal 12HUB).

The electrical cable terminals 12HUA and 12HUB constitute part of the first conductor 12U.

Reference numeral 12HLA is a terminal to which the cable end 21R of the second single-core wire 25A is connected (hereinbelow, it will be referred to as an electrical cable terminal 12HLA).

Reference numeral 12HLB is a terminal to which the cable end 21R of the second single-core wire 25B is connected (hereinbelow, it will be referred to as an electrical cable terminal 12HLB).

Reference numerals 12CA and 12CB are each a connection terminal to which a terminal of the condenser 60 is connected via solder (hereinbelow, it will be referred to as connection terminals 12CA and 12CB). The condenser 60 functions as a bypass condenser that connects the electrical cable terminal 12HLA to the electrical cable terminal 12HLB.

The electrical cable terminals 12HLA and 12HLB and the connection terminals 12CA and 12CB constitute part of the second conductor 12L.

Note that, although the configuration having the condenser 60 provided on the second surface 11L of the flexible substrate 10 is described in one or more embodiments, it is only necessary that the condenser 60 is formed on at least one surface of the first surface 11U and the second surface 11L of the flexible substrate 10, for example, a configuration having the condenser 60 provided on the first surface 11U may be adopted, or a configuration having the condenser 60 provided on both the first surface 11U and the second surface 11L. Moreover, a configuration in which the condenser 60 is not provided may be adopted.

Reference numerals 14A and 14B represent the through conductor 14 (hereinbelow, it will be referred to as through conductors 14A and 14B). The external conductor terminal 12JA is electrically connected to the electrical cable terminal 12HLA via the through conductor 14A. The external conductor terminal 12JB is electrically connected to the electrical cable terminal 12HLB via the through conductor 14B.

The first conductor 12U and the second conductor 12L formed on the flexible substrate 10 can be collectively formed by patterning using a known photolithographic technique or the like. Also, the through conductors 14A and 14B can also be formed by a known method.

(Signal Cable 30)

Figure 5:
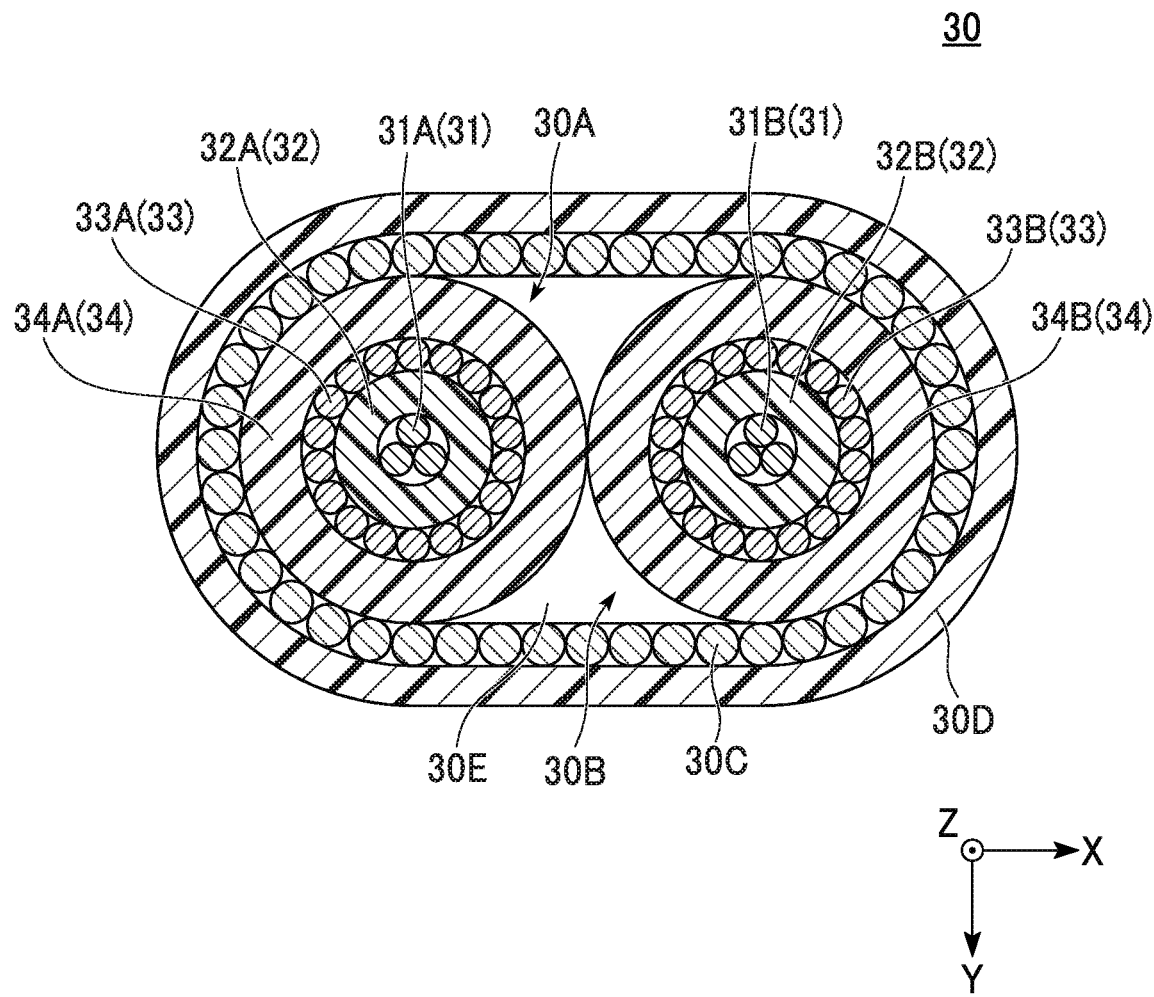
FIG. 5 is a cross-sectional view showing the signal cable constituting the imaging module according to one or more embodiments of the invention.

As shown in FIG. 5, the signal cable 30 includes two coaxial cables (a first coaxial cable 30A and a second coaxial cable 30B), a shield conductor 30C that surrounds the first coaxial cable 30A and the second coaxial cable 30B, and an outer coating 30D that surrounds the shield conductor 30C. The shield conductor 30C is provided on the entire inner peripheral surface of the outer coating 30D and is formed in a layer shape.

In FIG. 5, for example, the structure is shown in which the shield conductor 30C is disposed separately from a cable contact portion at which the side portions of the first coaxial cable 30A and the second coaxial cable 30B are in contact with each other, and a space 30E is present between the cable contact portion and the shield conductor 30C located at both sides of the cable contact portion. However, as a cross-sectional structure of the signal cable 30, a cross-sectional structure is applicable, in which the shield conductor 30C enters a region of the space 30E shown in FIG. 5 and a space is substantially absent among the first coaxial cable 30A, the second coaxial cable 30B, and the layer-shaped shield conductor 30C.

Each of the coaxial cables 30A and 30B includes an internal conductor 31 (31A, 31B), an internal insulator 32 (32A, 32B), an external conductor 33 (33A, 33B), and an external insulator 34 (34A, 34B). For example, the internal conductor 31 is used as a signal line that supplies a signal to the solid-state image sensing device 40, and the external conductor 33 is used as a power supply line that supplies electric power to the solid-state image sensing device 40.

As shown in FIGS. 4A, 4B, and 5, the internal conductor 31A is electrically connected to the internal conductor terminal 12IA. The external conductor 33A is electrically connected to the external conductor terminal 12JA. The internal conductor 31B is electrically connected to the internal conductor terminal 12IB. The external conductor 33B is electrically connected to the external conductor terminal 12JB.

Furthermore, in the aforementioned connection structure, the internal conductor 31A is electrically connected to the first image-sensing terminal 45A via the first conductor 12U (internal conductor terminal 12IA, the electrical cable terminal 12HUA) and the first single-core wire 24A.

The external conductor 33A is electrically connected to the second image-sensing terminal 46A via the external conductor terminal 12JA, the through conductor 14A, the second conductor 12L (electrical cable terminal 12HLA), and the second single-core wire 25A.

The internal conductor 31B is electrically connected to the first image-sensing terminal 45B via the first conductor 12U (internal conductor terminal 12IB, the electrical cable terminal 12HUB) and the first single-core wire 24B.

The external conductor 33B is electrically connected to the second image-sensing terminal 46B via the external conductor terminal 12JB, the through conductor 14B, the second conductor 12L (electrical cable terminal 12HLB), and the second single-core wire 25B.

According to the above-mentioned embodiments, it is possible to electrically connect the coaxial cables 30A and 30B to the image-sensing terminals 45 and 46 of the solid-state image sensing device 40 via the flexible substrate 10 and the single-core wire unit 20.

Moreover, the single-core wire unit 20 includes the plurality of the single-core wires 24 and 25 each having flexibility, the imaging module 1 can flexibly bend at ±90 degrees in the movable region 22 of the single-core wire unit 20. That is, in the case where the imaging module 1 is applied to a head-swing endoscope, it is possible to achieve a head-swing at ±90 degrees. Consequently, it is possible to achieve a head-swing endoscope that causes the movable region thereof to be less easily limited and is capable of carrying out a head-swing operation in a wider movable region.

Furthermore, since a rigid portion length of the imaging module 1 is approximately 2.2 mm, the rigid portion length can be shorter than a conventional rigid portion length (approximately 4.8 mm or approximately 4.1 mm). Accordingly, a head swing radius of the imaging module 1 becomes approximately 2.2 mm, and therefore it is possible to realize a head swing radius smaller than that of a conventional imaging module. In accordance with this, it is possible to use an endoscope provided with the imaging module in a further fine and narrow environment.

Additionally, the solders 15 to 18 and 47 are covered with the resists 13A, 13B, 13C, and 23, and therefore the strength of the electrical connection structure is reinforced by the solders 15 to 18 and 47. As a result, even in the case where the imaging module 1 is repeatedly bent with an increase in use frequency of the head-swing endoscope, the reliability of electrical connection due to the solders can be improved, and it is possible to prevent wire breakage.

Although the disclosure had been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. An imaging module comprising:
an image-sensing device comprising:
a light-receiving face;
a terminal surface located on the opposite side of the light receiving face; and
a terminal group having a first image-sensing terminal disposed on the terminal surface and a second image-sensing terminal also disposed on the terminal surface;
a flexible substrate that is separated from the image-sensing device and comprises:
a first surface;
a second surface on an opposite side of the first surface;
a first conductor disposed on the first surface; and
a second conductor disposed on the second surface;
a single-core wire unit that:
is disposed between the image-sensing device and the flexible substrate,
and
comprises:
a first flexible single-core wire that electrically connects the first image-sensing terminal to the first conductor; and
a second flexible single-core wire that electrically connects the second image-sensing terminal to the second conductor;
a through conductor; and
two coaxial cables disposed on the first surface and each comprising an internal conductor and an external conductor, wherein
the first and the second flexible single-core wires are connected to the first and the second image-sensing terminals, respectively,
the first conductor comprises:
an external conductor terminal to which the external conductor is connected, and
the through conductor penetrates the flexible substrate and electrically connects the external conductor terminal to the second conductor.

2. The imaging module according to claim 1, further comprising:
a first solder that connects the terminal group to the single-core wire unit;
a second solder that connects the single-core wire unit to the first and the second conductors; and
a third solder that connects the first and the second conductors to the coaxial cables.

3. The imaging module according to claim 2, further comprising:
a first resin that coats the first solder;
a second resin that coats the second solder; and
a third resin that coats the third solder.

4. The imaging module according to claim 1, wherein
the internal conductor is electrically connected to the first image-sensing terminal via the first conductor and the first single-core wire, and
the external conductor is electrically connected to the second image-sensing terminal via the external conductor terminal of the first conductor, the through conductor, the second conductor, and the second single-core wire.

5. The imaging module according to claim 1, further comprising
a condenser disposed on at least one of the first surface and the second surface.

6. The imaging module according to claim 1, wherein the single-core wire unit comprises a movable region where the flexible single-core wires bend at ±90 degrees with respect to an extending direction of the imaging module.

7. The imaging module according to claim 1, wherein each of the flexible single-core wires has a length of 1 cm to 5 cm.

8. The imaging module according to claim 1, wherein the first conductor further comprises:
an electrical cable terminal to which the first flexible single-core wire is connected; and
an internal conductor terminal to which the internal conductor is connected.

9. The imaging module according to claim 1, wherein the second conductor comprises:
an electrical cable terminal to which the second flexible single-core wire is connected; and
a connection terminal to which a condenser is connected.

* * * * *